(12) United States Patent
Hu et al.

(10) Patent No.: US 11,103,608 B1
(45) Date of Patent: Aug. 31, 2021

(54) MOBILE PRETREATMENT APPARATUS AND AN OPERATING METHOD THEREOF, AND A MOBILE ANALYSIS APPARATUS AND AN OPERATING METHOD THEREOF

(71) Applicants: Chio Kang Medical, Inc., Palo Alto, CA (US); Qiaokang Biotech (Guangdong) Co., LTD., Guangzhou (CN)

(72) Inventors: Shengwei Hu, Guangzhou (CN); Jianlong Xue, Guangzhou (CN); Dongxin Hou, Guangzhou (CN); Xuzhong Liao, Guangzhou (CN); Xin Yin, Guangzhou (CN); Guqun Ren, Guangzhou (CN); Xiuling Zhong, Guangzhou (CN); Yuhua Zou, Guangzhou (CN); Yecheng He, Guangzhou (CN); Ziping Zhu, Guangzhou (CN); Lixiong Feng, Palo Alto, CA (US)

(73) Assignees: Chio Kang Medical, Inc., Palo Alto, CA (US); Qiaokane Biotech (Guangdong) Co., LTD., Guangzhou (CN)

( * ) Notice: Subject to any disclaimer, the term of this patent is extended or adjusted under 35 U.S.C. 154(b) by 0 days.

(21) Appl. No.: 17/004,930

(22) Filed: Aug. 27, 2020

Related U.S. Application Data

(63) Continuation of application No. PCT/CN2020/100122, filed on Jul. 3, 2020.

(51) Int. Cl.
   *A61L 2/24* (2006.01)
   *A61L 2/07* (2006.01)
   (Continued)

(52) U.S. Cl.
   CPC .............. *A61L 2/24* (2013.01); *A61L 2/07* (2013.01); *A61L 2/206* (2013.01);
   (Continued)

(58) Field of Classification Search
   CPC ... A61L 2/24; A61L 2/07; A61L 2/206; A61L 2202/121; A61L 2202/16; A61L 2202/14;
   (Continued)

(56) References Cited

U.S. PATENT DOCUMENTS

| | | | |
|---|---|---|---|
| 1,954,056 | A | 4/1934 | Miller |
| 2,586,670 | A | 2/1952 | Lambertsen |

(Continued)

FOREIGN PATENT DOCUMENTS

| | | |
|---|---|---|
| CN | 1223166 A | 7/1999 |
| CN | 1397474 A | 2/2003 |

(Continued)

OTHER PUBLICATIONS

International Application No. PCT/CN2020/101140 as prepared by the Chinese International Searching Authority filed on Jul. 9, 2020, 59 pages.

(Continued)

*Primary Examiner* — Regina M Yoo
(74) *Attorney, Agent, or Firm* — Adsero IP

(57) ABSTRACT

The present disclosure discloses a mobile pretreatment method and apparatus, which may include: a vehicle-mounted system; and a detachable pretreatment chamber fluidly connected to the vehicle-mounted system. The detachable pretreatment chamber may be configured to accommodate an item for sterilization, and may include a temperature and humidity detector, a humidification device, and a water heating device. The vehicle-mounted system may be mountable on a vehicle, and may include an automatic control system, a heating system, a humidification (Continued)

system, and a water inlet system, the latter three being electrically connected to the automatic control system. The heating system may be fluidly connected to the water inlet system, and may be fluidly connected to the water heating device. The humidification system may be fluidly connected to the water inlet system, and may be fluidly connected to the humidification device. The present disclosure further discloses a mobile analysis apparatus and operating method thereof.

9 Claims, 9 Drawing Sheets

(51) Int. Cl.
    *A61L 2/20* (2006.01)
    *A61L 101/44* (2006.01)

(52) U.S. Cl.
    CPC ..... *A61L 2101/44* (2020.08); *A61L 2202/121* (2013.01); *A61L 2202/122* (2013.01); *A61L 2202/14* (2013.01); *A61L 2202/15* (2013.01); *A61L 2202/16* (2013.01)

(58) Field of Classification Search
    CPC ........... A61L 2202/122; A61L 2202/15; A61L 2101/44
    See application file for complete search history.

(56) References Cited

U.S. PATENT DOCUMENTS

| | | | |
|---|---|---|---|
| 2,817,689 A | 12/1957 | White | |
| 3,022,054 A | 2/1962 | Kotzebue | |
| 3,598,543 A | 6/1969 | Crosby et al. | |
| 3,572,391 A | 3/1971 | Hirsch et al. | |
| 3,844,739 A | 10/1974 | Alfrey, Jr. | |
| 3,961,920 A | 6/1976 | Gilbert | |
| 3,997,633 A | 12/1976 | Leva et al. | |
| 4,112,054 A | 9/1978 | Feingold et al. | |
| 4,119,539 A | 10/1978 | Ettel et al. | |
| 4,134,425 A | 1/1979 | Gussefeld et al. | |
| 4,243,636 A | 1/1981 | Shiraki et al. | |
| 4,301,113 A | 11/1981 | Alguire et al. | |
| 4,517,167 A | 5/1985 | Popescu et al. | |
| 4,549,363 A | 10/1985 | Buonicore | |
| 4,555,251 A | 11/1985 | Jonsson | |
| 4,831,196 A | 5/1989 | Buonicore et al. | |
| 5,084,075 A | 1/1992 | Sircar | |
| 5,204,075 A | 4/1993 | Jain et al. | |
| 5,270,000 A | 12/1993 | Goldner et al. | |
| 5,283,035 A | 2/1994 | Karthaus et al. | |
| 5,290,345 A | 3/1994 | Osendorf et al. | |
| 5,511,409 A | 4/1996 | Knaebel | |
| 5,522,808 A | 6/1996 | Skalla | |
| 5,607,652 A | 3/1997 | Hellmuth et al. | |
| 5,641,455 A | 6/1997 | Rosenlund et al. | |
| 5,702,669 A | 12/1997 | Green et al. | |
| 5,741,470 A | 4/1998 | Wenzler | |
| 5,755,857 A | 5/1998 | Acharya et al. | |
| 5,779,773 A | 7/1998 | Cam et al. | |
| 5,964,927 A | 10/1999 | Graham et al. | |
| 6,156,101 A | 12/2000 | Naheiri | |
| 6,684,648 B2 * | 2/2004 | Faqih .................. | E03B 3/28 62/93 |
| 6,743,402 B2 | 6/2004 | Shimakawa | |
| 7,316,733 B1 | 1/2008 | Hedrick | |
| 7,625,535 B2 | 12/2009 | Yamaguchi | |
| 8,431,085 B2 | 4/2013 | Froderberg et al. | |
| 9,616,143 B2 | 4/2017 | Snyder et al. | |
| 10,987,443 B1 | 4/2021 | Hu et al. | |
| 2002/0046569 A1 * | 4/2002 | Faqih .................. | C02F 9/005 62/188 |
| 2002/0197194 A1 | 12/2002 | Machado et al. | |
| 2005/0145108 A1 | 7/2005 | Rubin | |
| 2006/0236860 A1 | 10/2006 | Sumida et al. | |
| 2006/0249027 A1 | 11/2006 | Adolphsen et al. | |
| 2007/0209383 A1 * | 9/2007 | Hutton .................. | B64F 1/364 62/434 |
| 2008/0078289 A1 | 4/2008 | Sergi et al. | |
| 2008/0080999 A1 | 4/2008 | Bondar | |
| 2010/0196194 A1 | 8/2010 | Voeten et al. | |
| 2011/0265644 A1 | 11/2011 | Swami et al. | |
| 2011/0283885 A1 | 11/2011 | Thiele | |
| 2012/0031268 A1 | 2/2012 | Yaghi et al. | |
| 2012/0298207 A1 | 11/2012 | Woelk et al. | |
| 2014/0119989 A1 | 5/2014 | Hayashi | |
| 2014/0251130 A1 | 9/2014 | Sprinkle et al. | |
| 2014/0290162 A1 | 10/2014 | Tanimoto | |
| 2016/0010883 A1 | 1/2016 | Jomitz et al. | |
| 2017/0056813 A1 | 3/2017 | McMahon et al. | |
| 2019/0076776 A1 | 3/2019 | Mahecha-Botero et al. | |
| 2019/0151791 A1 | 5/2019 | Awadh et al. | |

FOREIGN PATENT DOCUMENTS

| | | |
|---|---|---|
| CN | 101224381 A | 7/2008 |
| CN | 101549241 A | 10/2009 |
| CN | 101773762 A | 7/2010 |
| CN | 201632182 U | 11/2010 |
| CN | 102173384 A | 9/2011 |
| CN | 102219642 A | 10/2011 |
| CN | 102302791 A | 1/2012 |
| CN | 102921570 A | 2/2013 |
| CN | 202802975 U | 3/2013 |
| CN | 202933710 U | 5/2013 |
| CN | 203183363 U | 9/2013 |
| CN | 103386141 A | 11/2013 |
| CN | 103394109 A | 11/2013 |
| CN | 103394278 A | 11/2013 |
| CN | 103657383 A | 3/2014 |
| CN | 103706233 A | 4/2014 |
| CN | 203507806 U | 4/2014 |
| CN | 203564952 U | 4/2014 |
| CN | 103800926 A | 5/2014 |
| CN | 103908688 A | 7/2014 |
| CN | 203749877 U | 8/2014 |
| CN | 203750388 U | 8/2014 |
| CN | 203750389 U | 8/2014 |
| CN | 104014227 A | 9/2014 |
| CN | 104275085 A | 1/2015 |
| CN | 104307008 A | 1/2015 |
| CN | 204261680 U | 4/2015 |
| CN | 204447972 U | 7/2015 |
| CN | 104815535 A | 8/2015 |
| CN | 105132060 A | 12/2015 |
| CN | 105327665 A | 2/2016 |
| CN | 105664822 A | 2/2016 |
| CN | 205300112 U | 6/2016 |
| CN | 210721130 U | 6/2016 |
| CN | 106139199 A | 11/2016 |
| CN | 106421844 A | 2/2017 |
| CN | 106475021 A | 3/2017 |
| CN | 106582126 A | 4/2017 |
| CN | 206443946 U | 8/2017 |
| CN | 206535551 U | 10/2017 |
| CN | 206853397 U | 1/2018 |
| CN | 107677016 A | 2/2018 |
| CN | 207169397 U | 4/2018 |
| CN | 207187436 U | 4/2018 |
| CN | 207356290 U | 5/2018 |
| CN | 207745676 U | 8/2018 |
| CN | 207913454 U | 9/2018 |
| CN | 108607511 A | 10/2018 |
| CN | 208047841 U | 11/2018 |
| CN | 208218734 U | 12/2018 |
| CN | 109302064 A | 2/2019 |
| CN | 208448985 U | 2/2019 |
| CN | 208893903 U | 5/2019 |
| CN | 110145747 A | 8/2019 |
| CN | 110302634 A | 10/2019 |
| CN | 110404485 A | 11/2019 |
| CN | 110461371 A | 11/2019 |

(56) References Cited

FOREIGN PATENT DOCUMENTS

| | | |
|---|---|---|
| CN | 209662917 U | 11/2019 |
| CN | 110833754 A | 2/2020 |
| CN | 210021633 U | 2/2020 |
| CN | 210088451 U | 2/2020 |
| DE | 4236622 C1 | 3/1994 |
| EP | 0130319 A2 | 1/1985 |
| EP | 0350677 A1 | 1/1990 |
| EP | 1302478 A1 | 4/2003 |
| EP | 2883598 A1 | 6/2015 |
| GB | 1472091 A | 4/1977 |
| JP | 2008114210 A | 5/2008 |
| JP | 2013172790 A | 10/2016 |
| JP | 2010259648 A | 5/2018 |
| WO | WO2011002277 A1 | 1/2011 |
| WO | WO-2019-136504 A1 | 7/2019 |
| WO | WO2019236249 A1 | 12/2019 |

OTHER PUBLICATIONS

U.S. Appl. No. 17/012,857, TrackOne Bypass CON Application filed Sep. 4, 2020, 148 pages.
International Application No. PCT/CN2020/100143 as prepared by the Chinese International Searching Authority filed on Jul. 3, 2020, 25 pages.
U.S. Appl. No. 17/002,500, TrackOne Bypass CON Application filed Aug. 25, 2020, 61 pages.
International Application No. PCT/CN2020/100125 as prepared by the Chinese International Searching Authority filed on Jul. 3, 2020, 27 pages.
U.S. Appl. No. 17/002,523, TrackOne Bypass CON Application filed Aug. 25, 2020, 72 pages.
U.S. Appl. No. 17/002,523 Non-Final Office Action, dated Oct. 27, 2020, 54 pages.
International Application No. PCT/CN2020/100115 as prepared by the Chinese International Searching Authority filed on Jul. 3, 2020, 22 pages.
U.S. Appl. No. 17/002,529, TrackOne Bypass CON Application filed Aug. 25, 2020, 64 pages.
International Application No. PCT/CN2020/100119 as prepared by the Chinese International Searching Authority filed on Jul. 3, 2020, 29 pages.
U.S. Appl. No. 17/002,540, TrackOne Bypass CON Application filed Aug. 25, 2020, 89 pages.
International Application No. PCT/CN2020/100120 as prepared by the Chinese International Searching Authority filed on Jul. 3, 2020, 28 pages.
U.S. Appl. No. 17/004,730, TrackOne Bypass CON Application filed Aug. 27, 2020, 77 pages.
International Application No. PCT/CN2020/101142 as prepared by the Chinese International Searching Authority filed on Jul. 9, 2020, 29 pages.
U.S. Appl. No. 17/012,864, TrackOne Bypass CON Application filed Sep. 4, 2020, 78 pages.
International Application No. PCT/CN2020/100144 as prepared by the Chinese International Searching Authority filed on Jul. 3, 2020, 24 pages.
U.S. Appl. No. 17/004,903, TrackOne Bypass CON Application filed Aug. 27, 2020, 67 pages.
U.S. Appl. No. 17/004,903 Notice of Allowance, dated Nov. 6, 2020, 19 pages.
International Application No. PCT/CN2020/100122 as prepared by the Chinese International Searching Authority filed on Jul. 3, 2020, 34 pages.
International Application No. PCT/CN2020/100113 as prepared by the Chinese International Searching Authority filed on Jul. 3, 2020, 35 pages.
U.S. Appl. No. 17/004,971, TrackOne Bypass CON Application filed Aug. 27, 2020, 75 pages.
U.S. Appl. No. 17/012,857, Non-Final Office Action, dated Nov. 24, 2020, 13 pages.
U.S. Appl. No. 17/002,540, Office Action-Restriction Requirement, dated Dec. 1, 2020, 7 pages.
U.S. Appl. No. 17/002,500, Non-Final Office Action dated Dec. 8, 2020, 109 pages.
Kahm et al., 2018 "Lyapunov exponents with Model Predictive Control for exothermic batch reactors" IFAC—PapersOnline, 51, 417-422.
U.S. Appl. No. 17/004,971, Office Action—Restriction Requirement, dated Dec. 9, 2020, 6 pages.
U.S. Appl. No. 17/002,523 Notice of Allowance, dated Dec. 17, 2020, 35 pages.
U.S. Appl. No. 17/002,540, Non-Final Office Action dated Dec. 30, 2020, 62 pages.
International Search Report and Written Opinion, International Application No. PCT/CN2020/101140 dated Dec. 21, 2020, 11 pages.
International Search Report and Written Opinion, International Application No. PCT/CN2020/100143 dated Dec. 21, 2020, 9 pages.
International Search Report and Written Opinion, International Application No. PCT/CN2020/100125 dated Dec. 23, 2020, 9 pages.
International Search Report and Written Opinion, International Application No. PCT/CN2020/100115 dated Dec. 16, 2020, 11 pages.
International Search Report and Written Opinion, International Application No. PCT/CN2020/100119 dated Dec. 17, 2020, 9 pages.
International Search Report and Written Opinion, International Application No. PCT/CN2020/101142 dated Dec. 16, 2020, 11 pages.
International Search Report and Written Opinion, International Application No. PCT/CN2020/100144 dated Dec. 18, 2020, 10 pages.
U.S. Appl. No. 17/002,500, Final Office Action dated Feb. 8, 2021, 57 pages.
U.S. Appl. No. 17/004,971, Notice of Allowance, dated Feb. 8, 2021, 30 pages.
U.S. Appl. No. 17/002,529, Non-Final Office Action—Restriction Requirement dated Feb. 17, 2021, 11 pages.
U.S. Appl. No. 17/012,857, Notice of Allowance, dated Mar. 1, 2021, 26 pages.
U.S. Appl. No. 17/002,540, Final Office Action, dated on Mar. 26, 2021,3 36 pages.
U.S. Appl. No. 17/004,730, Non-Final Office Action, dated Apr. 1, 2021, 30 pages.
U.S. Appl. No. 17/002,500, Non-Final Office Action dated Apr. 14, 2021, 89 pages.
U.S. Appl. No. 17/002,540, Notice of Allowance, dated Apr. 26, 2021, 21 pages.
International Search Report & Written Opinion for PCT/CN2020/100113 as prepared by the Chinese International Searching Authority dated Mar. 31, 2021, 10 pages.
International Search Report & Written Opinion for PCT/CN2020/100122 as prepared by the Chinese International Searching Authority dated Mar. 26, 2021, 11 pages.
International Search Report & Written Opinion for PCT/CN2020/100120 as prepared by the Chinese International Searching Authority dated Mar. 31, 2021, 10 pages.
U.S. Appl. No. 17/004,903 Notice of Allowance, dated May 17, 2021, 20 pages.
U.S. Appl. No. 17/002,529 Notice of Allowance, dated May 3, 2021, 30 pages.
U.S. Appl. No. 17/002,523 Notice of Allowance, dated May 27, 2021, 26 pages.
U.S. Appl. No. 17/012,864, Notice of Allowance, dated Jun. 15, 2021, 56 pages.
U.S. Appl. No. 17/004,730, Notice of Allowance, dated Jun. 24, 2021, 30 pages.
U.S. Appl. No. 17/012,857, Notice of Allowance, dated Jun. 28, 2021, 21 pages.

(56) References Cited

OTHER PUBLICATIONS

U.S. Appl. No. 17/002,500, Notice of Allowance dated Jul. 8, 2021, 27 pages.

* cited by examiner

MOBILE PRETREATMENT APPARATUS AND AN OPERATING METHOD THEREOF, AND A MOBILE ANALYSIS APPARATUS AND AN OPERATING METHOD THEREOF

CROSS-REFERENCE TO RELATED PATENT APPLICATIONS

This application is a continuation of International Application No. PCT/CN2020/100122, filed on Jul. 3, 2020, which is incorporated herein by reference in its entirety for all purposes.

TECHNICAL FIELD

The present disclosure relates to the technical field of sterilization technology, and more particularly, to a mobile pretreatment apparatus and an operating method thereof, and a mobile analysis apparatus and an operating method thereof.

BACKGROUND

Ethylene oxide ("EO") is a broad-spectrum, highly effective sterilizer. Ethylene oxide low temperature sterilization is a sterilization process that is currently widely used.

The ethylene oxide sterilization process includes the three steps of pretreatment, sterilization, and analysis. The ethylene oxide sterilization process directly affects the sterilization effect of items, and the involved equipment, methods, operations, and use management have their own special requirements. The pretreatment of items to be sterilized is also one of the factors that affect the sterilization effect of products.

At present, existing technologies mainly adopt a pretreatment chamber for pre-heating and pre-humidifying products. The pretreatment chamber and the sterilization chamber have the same volume. After pre-heating, the product is transferred to an EO sterilization chamber for sterilization operation. Such a process is a single batch treating process, and since pre-heating time and sterilization time required by the products are different, a certain step has to be performed before the next step, which results in no-load and waste in equipment. There are also systems and operating methods that do not provide a pretreatment chamber but perform a sterilization procedure after pretreatment in an ethylene oxide sterilizer. Although this operating method omits the pretreatment chamber, the sterilization time will be greatly extended. At the same time, the next round of sterilization cannot be performed immediately after each sterilization, and the period required is longer. In addition, at present, all pretreatment apparatuses in the prior art are fixed sealed containers, and there is no mobile pretreatment chamber and apparatus for ethylene oxide sterilization items, which is not convenient for the promotion and development of ethylene oxide sterilization.

For the step of analysis, there are currently two safer analysis methods: (1) adopting an EO sterilizer, which adopts an equipment encompassing functions of double-cycle sterilization and ventilation, and the analysis can be continued in the EO sterilization cabinet; and (2) putting the sterilized items into a special ventilation cabinet to continue the analysis under ventilation after sterilization.

Existing research shows that under normal storage conditions, most items that have been fumigated with ethylene oxide have a residual ethylene oxide content of less than 1 ppm after 14 days. The analyzing speed of ethylene oxide accelerates with the increase in ventilation quantity and temperature. The EO sterilized items used in hospitals are mostly precision or expensive instruments, especially some intervention materials, which have less backup and high frequency of use. In order to meet clinical needs, it is necessary to make full use of limited resources and to pay attention to the use of those resources in a safe manner. The analysis of items subjected to EO sterilization and disinfection must be treated with mechanical ventilation or using a special ventilation cabinet. Natural ventilation cannot be used to remove residual EQ. Since the ethylene oxide sterilization and analysis apparatuses in hospitals or the like are generally larger-volume equipment, the items to be sterilized need to be transported for sterilization and analysis, which is inconvenient.

Therefore, how to realize the simple setting and rapid movement of the pretreatment apparatus and the analysis apparatus for ethylene oxide sterilization is a problem that those skilled in the art need to solve urgently.

Hence, there may be a need for more robust and scalable solutions for implementing sterilization technologies, and, more particularly, for implementing a mobile pretreatment apparatus and an operating method thereof, and implementing a mobile analysis apparatus and an operating method thereof.

SUMMARY

The present disclosure provides a mobile pretreatment apparatus including: a vehicle-mounted system; and a detachable pretreatment chamber that is fluidly connected to the vehicle-mounted system through a first pipeline. The detachable pretreatment chamber may be configured to accommodate an item to be sterilized, and may be provided with a temperature and humidity detector, a humidification device, and a water heating device. The vehicle-mounted system may be adapted to be mounted on a vehicle, and may include a heating system, a humidification system, a water inlet system, and an automatic control system. The heating system, the humidification system, and the water inlet system may each be electrically connected to the automatic control system. The heating system may be fluidly connected to the water inlet system through a second pipeline, and may be fluidly connected to the water heating device through a third pipeline. The humidification system may be fluidly connected to the water inlet system through a fourth pipeline, and may be fluidly connected to the humidification device through a fifth pipeline.

The present disclosure further provides a method of operating the mobile pretreatment apparatus as described above, including the steps of:

S1: fluidly connecting the water inlet system to an external water source, after the vehicle that is loaded with the vehicle-mounted system arrives at a designated location, so that water may be input into the heating system through the water inlet system for heating;

S2: building the detachable pretreatment chamber near the vehicle-mounted system; mounting the temperature and humidity detector, the water heating device, and the humidification device in the detachable pretreatment chamber; fluidly connecting the humidification device to the humidification system of the vehicle-mounted system through a fourth pipeline; and fluidly connecting the water heating device to the heating system of the vehicle-mounted system through a third pipeline;

S3: placing items to be sterilized in the detachable pretreatment chamber; circulating water between the heating system and the water heating device to heat the detachable pretreatment chamber; using the humidification system to humidify the detachable pretreatment chamber through use of the humidification device; and S4: monitoring temperature and humidity in the detachable pretreatment chamber in real time using the temperature and humidity detector, and transmitting the monitored temperature and humidity measurements to the automatic control system, so that the automatic control system can control the humidification device and the water heating device to maintain the detachable pretreatment chamber at a predetermined temperature and humidity depending on the different items to be sterilized.

The present disclosure further provides a mobile analysis apparatus, including: a detachable analysis chamber configured to accommodate items to be analyzed; and a vehicle-mounted system adapted to be mounted on a vehicle. The vehicle-mounted system may include an automatic control system, a harmless gas treatment system, and a fresh air system. The harmless gas treatment system and the fresh air system may each be electrically connected to the automatic control system. The harmless gas treatment system may include a harmless gas treatment device. The detachable analysis chamber may be fluidly connected to the harmless gas treatment device through an exhaust pipe, and may be fluidly connected to the fresh air system through an intake pipe.

The present disclosure further provides a method of operating the mobile analysis apparatus as described above, including the steps of:

S1: building the detachable analysis chamber near the vehicle-mounted system, after the vehicle that is loaded with the vehicle-mounted system arrives at a designated location; fluidly connecting the harmless gas treatment system with the detachable analysis chamber through the exhaust pipe; and fluidly connecting the fresh air system with the detachable analysis chamber through the intake pipe;

S2: placing the sterilized items to be analyzed in the detachable analysis chamber; drawing the analysis gas from the detachable analysis chamber into the harmless gas treatment device; and directing sterile air of the fresh air system to flow into the detachable analysis chamber;

S3: harmlessly treating the analysis gas by using the harmless gas treatment device; discharging residual gas from the harmless gas treatment device, after the residual gas has been treated.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 1:
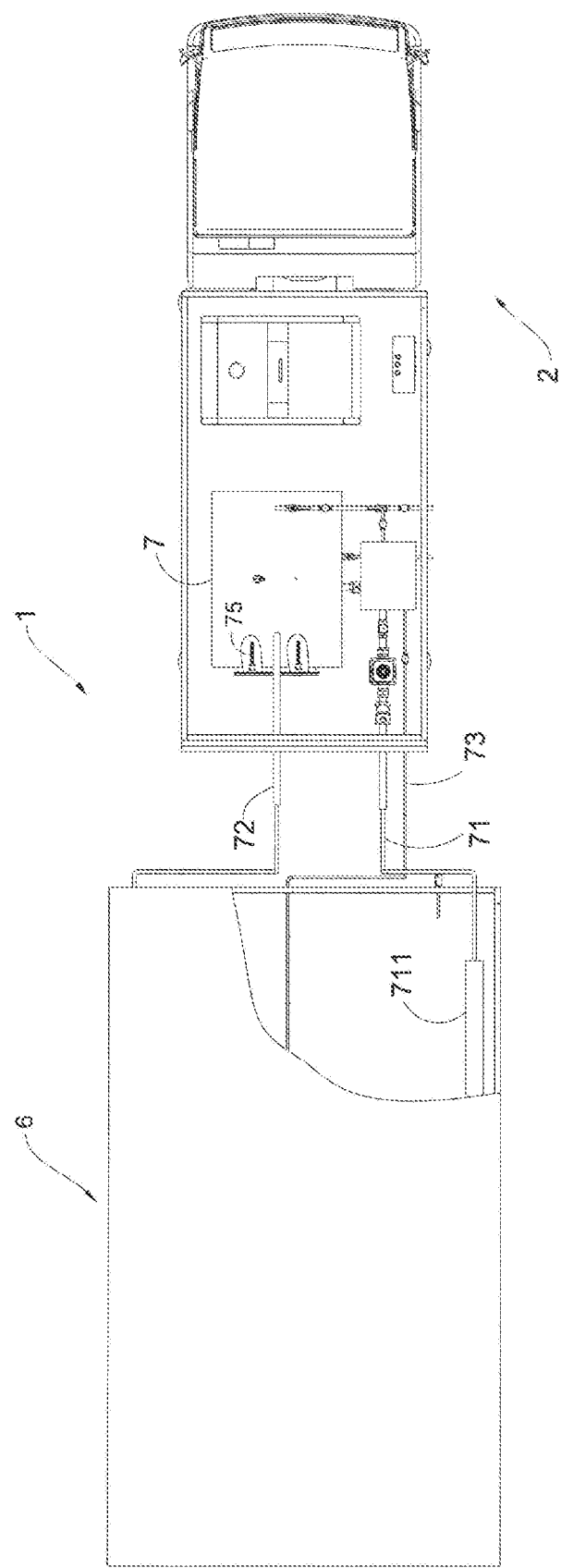
FIG. 1 is a schematic diagram depicting a top view of an internal structure of a mobile pretreatment apparatus according to an embodiment of the present disclosure.
Figure 2:
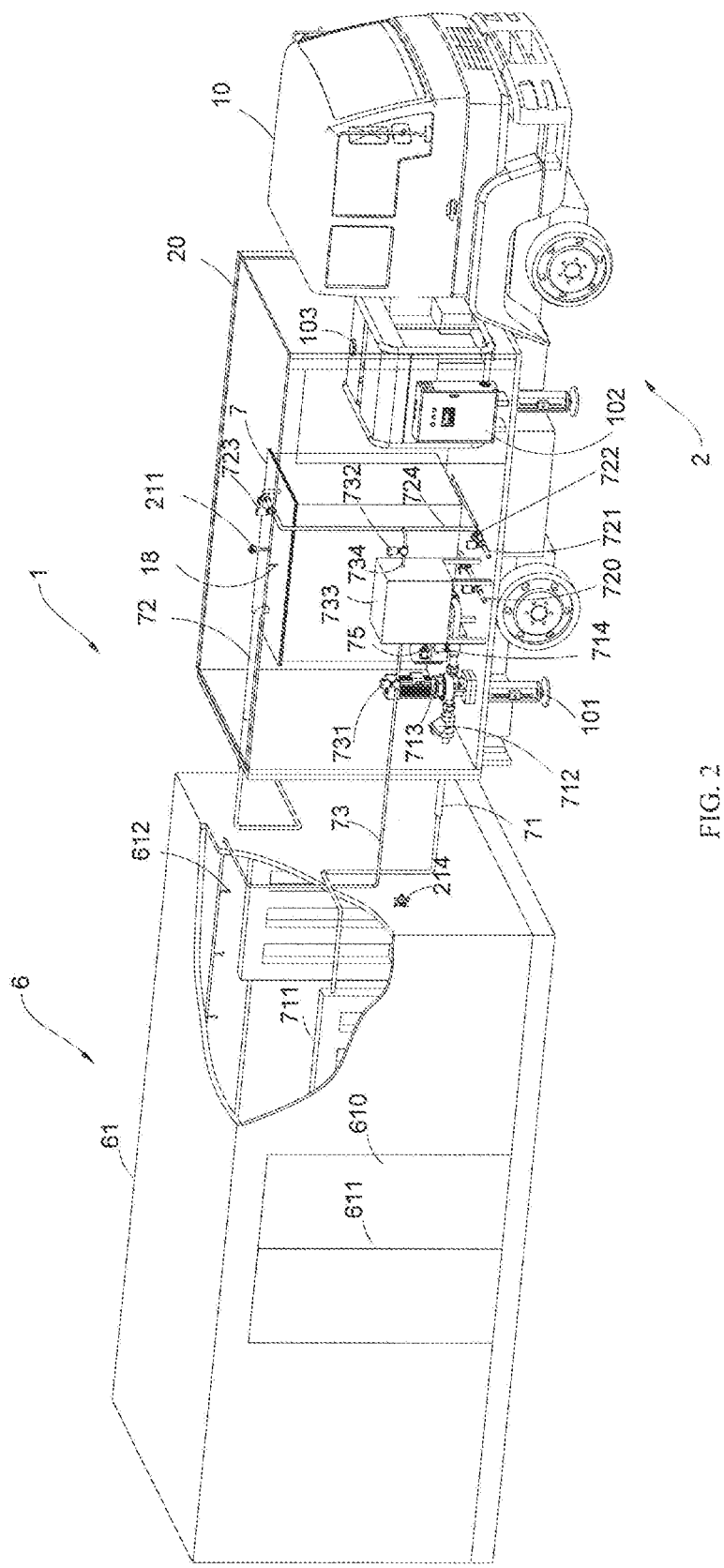
FIG. 2 is a schematic diagram depicting a perspective view of the mobile pretreatment apparatus of FIG. 1.
Figure 3:
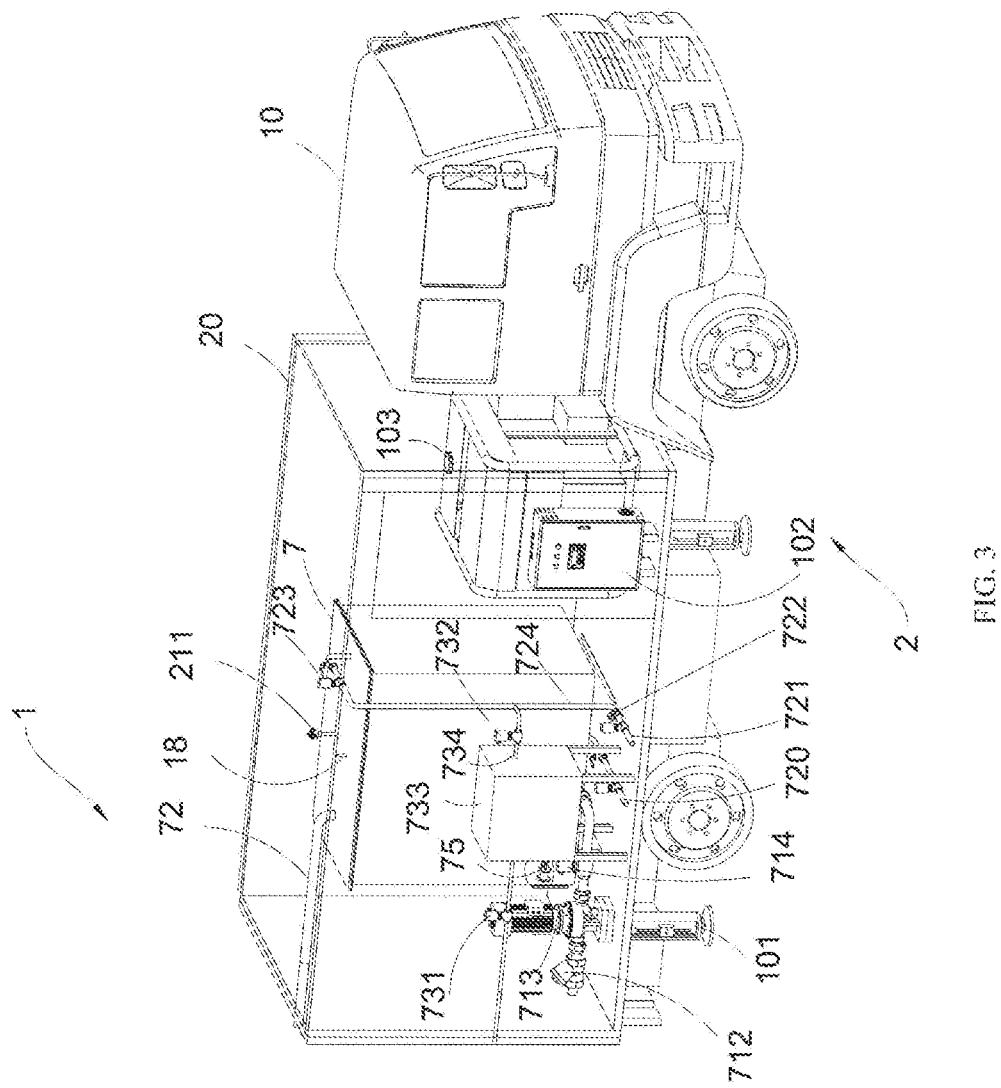
FIG. 3 is a schematic diagram depicting an enlarged view of a vehicle-mounted system of the mobile pretreatment apparatus of FIG. 2.
Figure 4:
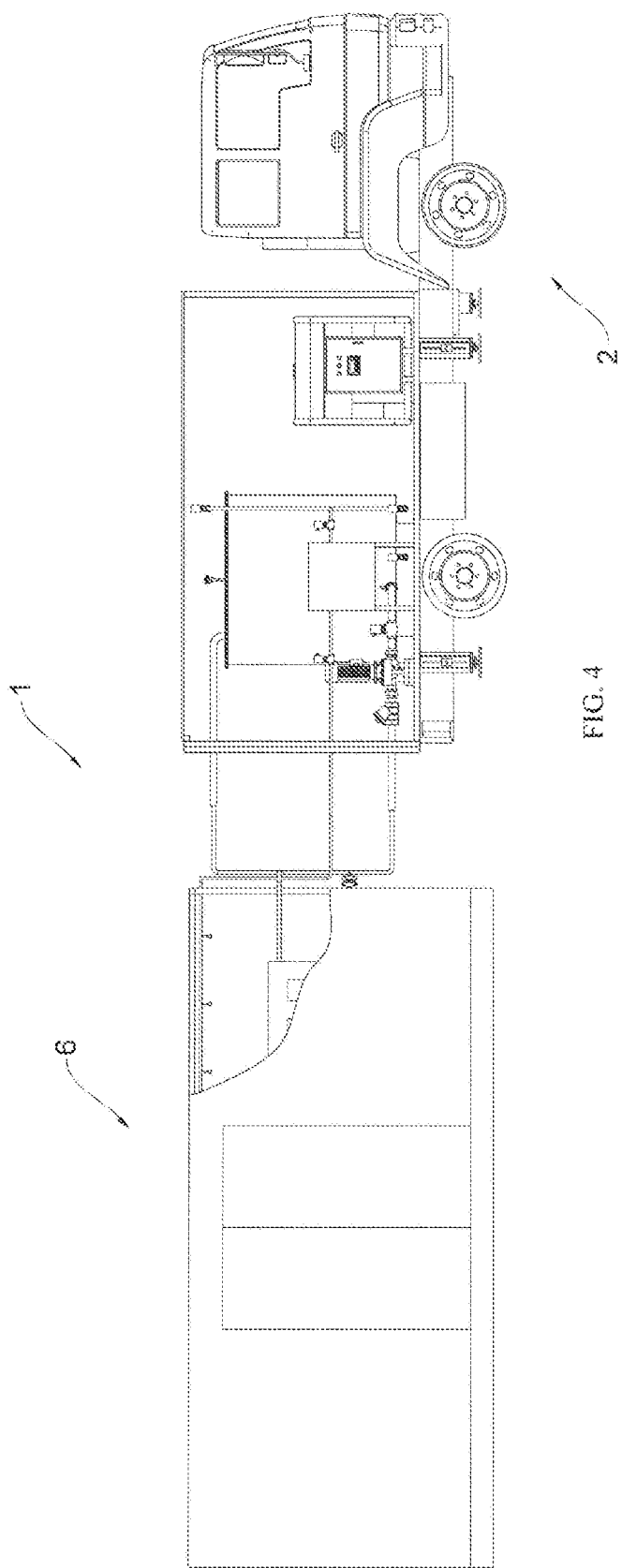
FIG. 4 is a schematic diagram depicting a side view of the mobile pretreatment apparatus of FIG. 1

As shown in FIGS. 1 to 4, an embodiment of the present disclosure discloses a mobile pretreatment apparatus 1. The mobile pretreatment apparatus 1 can be configured to pretreat items that are to be sterilized using ethylene oxide, but is not limited to such functionality. The mobile pretreatment apparatus 1 may include a detachable pretreatment chamber 6 and a vehicle-mounted system 20. The detachable pretreatment chamber 6 (also referred to herein as "sterilization pretreatment chamber 6" or simply "pretreatment chamber 6" or the like) may be a detachable and assemblable (or assemble-able) system, which may be configured to contain the items to be sterilized and may be provided with a temperature and humidity detector 214, a humidification device, and a water heating device. The detachable pretreatment chamber 6 can fluidly connect with the vehicle-mounted system 20 through a first pipeline (e.g., at least one of water inlet pipe 71, water return pipe 72, and/or humidification pipe 73, or the like). In some alternative embodiments, the vehicle-mounted system 20 and the detachable pretreatment chamber 6 can be directly connected to each other through one or more flanges. The vehicle-mounted system 20 may be a movable system, and may be adapted to be mounted on a vehicle, such as vehicle 2, or the like.

According to some embodiments, vehicle 2 may include, for example, the vehicle-mounted system 20 and a driving system 10. In some implementations, the vehicle-mounted system 20 may be mounted on the vehicle 2. The vehicle-mounted system 20 may be adapted to be driven by the driving system 10. The humidification device may include, but is not limited to, at least one humidification sprinkler 612, or the like. The water heating device may include, without limitation, at least one water heating plate 711, or the like. In an embodiment, the detachable pretreatment chamber 6 may include, but is not limited to, a pretreatment chamber body 61, at least one sealing strip 611, and at least one feed door 610. In the detachable pretreatment chamber 6 that has been assembled, the temperature and humidity detector 214, the at least one water heating plate 711, and the at least one humidification sprinkler 612 may be mounted in the pretreatment chamber body 61. The at least one water heating plate 711 may be located at a bottom interior portion of the pretreatment chamber body 61. The at least one humidification sprinkler 612 may be mounted at a top interior portion of the pretreatment chamber body 61. The pretreatment chamber body 61 may be composed of a plurality of splice plates. The at least one feed door 610 may be mounted on a side wall of the pretreatment chamber body 61, and may be configured to form a sealed closed space with the pretreatment chamber body 61 by using the at least one sealing strip 611.

In some embodiments, the at least one sealing strip 611 may each include, but is not limited to, a thermoplastic rubber sealing strip, which has good thermal insulation, high temperature resistance, and good flexibility. According to some embodiments, the pretreatment chamber body 61 may be a reusable thermal insulation material. The splice plates may be assembled by splicing to form the wall of the sterilization pretreatment chamber 6, without a column structure.

The vehicle-mounted system 20 may include a heating system, a humidification system, and a water inlet system. The heating system may be fluidly connected with the water inlet system through a second pipeline (e.g., water intake pipe 724, or the like), and may be fluidly connected with the water heating device (such as the at least one water heating plate 711, or the like) through a third pipeline (e.g., water inlet pipe 71, or the like). The heating system may specifically include a water tank 7 and a heater (including, without limitation, electric heating tube(s) 75, or other water heating device, or the like). The heater may be configured to heat water contained in the water tank 7. The water tank 7 might fluidly couple with the at least one water heating plate 711 through the water inlet pipe (e.g., water inlet pipe 71, or the like) and a water return pipe (e.g., water return pipe 72, or the like). The humidification system may be fluidly connected with the water inlet system through a fourth pipeline (e.g., replenishment pipe 734, or the like), and may be configured to connect with a humidification device (such as the at least one humidification sprinkler 612, or the like) through a fifth pipeline (e.g., humidification pipe 73, or the like). The humidification system may specifically include an atomizer replenishment pipe 734, an atomizer 733, and a humidification pipe 73 that are fluidly connected in sequence. The humidification pipe 73 may be in fluid communication with the at least one humidification sprinkler 612.

In some embodiments, the vehicle-mounted system 20 may further include an automatic control system. The temperature and humidity detector 214, the heating system, the humidification system, and the water inlet system may each be electrically connected to the automatic control system, and may be powered and controlled automatically through the automatic control system. The automatic control system may include a controller 102 and a power supply system 103. Specifically, the temperature and humidity detector 214 may be electrically connected to the controller 102.

The vehicle-mounted system 20 may further include a cargo box that can be loaded on a truck, and the heating system, the humidification system, and the water inlet system may be provided in the cargo box.

In some embodiments, the vehicle 2 may further include at least one supporting device 101. The at least one supporting device(s) 101 may be configured to be fixedly connected to a bottom portion of the vehicle-mounted system 20—specifically in some cases, mounted at four corners of the bottom portion of the vehicle-mounted system 20—to provide support for the vehicle-mounted system 20, and to maintain stability of the vehicle-mounted system 20 during operation.

In an embodiment, the heating system may include a heater (including, but not limited to, an electric heating tube(s) 75, other water heater devices, or the like), a water tank 7, a thermometer 211, a level gauge 18, a circulating water pump 713, a second filter 712, a fourth valve 714, a water inlet pipe 71, and a water return pipe 72. The water inlet pipe 71 may be fluidly connected between a water outlet of the water tank 7 and the at least one water heating plate 711. The fourth valve 714, the circulating water pump 713, and the second filter 712 may be sequentially provided on the water inlet pipe 71 in the direction from the water tank 7 to the at least one water heating plate 711. The water return pipe 72 may be fluidly connected between a water return port of the water tank 7 and the at least one water heating plate 711. The fourth valve 714 and the circulating water pump 713 may each be electrically connected to the controller 102 of the automatic control system. The heater may be configured to heat the water tank 7. For example, the electric heating tube(s) 75 may be inserted into a bottom interior portion of the water tank 7, and may be electrically connected to a power supply system 103 of the automatic control system. The thermometer 211 and the level gauge 18 may be mounted in the water tank 7, for example, in the middle-upper portion of the inner side wall (or the middle part of a top portion, or the like) of the water tank 7, and may be electrically connected to the controller 102. The water tank 7 may be fluidly connected to the water inlet system through a sixth pipeline (e.g., water intake pipe 724, or the like). In some embodiments, the electric heating tube(s) 75 may each be a stainless-steel electric heating tube, may be antiseptic, may be electrically connected with the automatic control system, and may be electrically connected with a power regulator. The heating power of the electric heating tube(s) 75 may be controlled by the controller 102.

According to some embodiments, the at least one water heating plate 711 may preferably include, without limitation, one of a copper-aluminum composite radiator or a steel-aluminum composite radiator, each of which has good corrosion resistance, has good thermal conductivity, and can save space.

In some embodiments, the controller 102 has a display. The controller 102 may display and process the monitoring data obtained by the temperature and humidity detector 214, the thermometer 211, and the level gauge 18 on the display in real time, and may perform parameter setting and program adjustment. The power supply system 103 may be a diesel generator, which serves as a mobile power supply for providing real-time power.

According to some embodiments, the thermometer 211 may be electrically connected to the controller 102. The controller 102 may be electrically connected to and may control the electric heating tube(s) 75 to achieve heating and temperature control of the water tank 7, so that the water tank 7 can maintain a constant temperature after reaching the setting temperature. The controller 102 may control and adjust the heating power of the electric heating tube(s) 75 according to the temperature fed back by the thermometer 211, and may achieve heating and temperature control of the water tank 7.

In some embodiments, the humidification system may include a humidification pipe 73, a first valve 731, an atomizer 733, and an atomizer replenishment pipe 734. The atomizer 733 may be fluidly connected to the water inlet system through the atomizer replenishment pipe 734, and may be fluidly connected to at least one humidification sprinkler 612 through the humidification pipe 73. The first valve 731 may be provided on the humidification pipe 73. The first valve 731 may be electrically connected to the controller 102. In some embodiments, the atomizer 733 has inlet pressure and discharge pressure, and can draw in water introduced into the atomizer replenishment pipe 734. After being atomized by the atomizer 733, the atomized water may be directed to flow into the pretreatment chamber body 61 via the humidification pipe 73.

In some embodiments, the water inlet system may include a water inlet 721, a first filter 722, a second valve 732, and a third valve 723. The water inlet 721 may be fluidly connected to each of the second valve 732 and the third valve 723 through the first filter 722 and through a seventh pipeline (e.g., water intake pipe 724, or the like). The second valve 732 may be fluidly connected to the atomizer replenishment pipe 734, and may be fluidly connected to the humidification system (e.g., the atomizer 733, or the like) through an eighth pipeline (e.g., the atomizer replenishment pipe 734, or the like). The third valve 723 may be fluidly connected to the water tank 7, and may be fluidly connect to the heating system (e.g., electric heating tube(s) 75 disposed in the water tank 7, or the like) through a ninth pipeline (e.g., water intake pipe 724, or the like). The second valve 732 and the third valve 723 may be electrically connected to the controller 102.

In an embodiment, the water inlet 721 may be a quick-connect snap connector, which may be configured to directly connect with a water pipe of an external water source, or the like.

An embodiment of the present disclosure provides a method of operating the abovementioned mobile pretreatment apparatus 1, and a non-limiting example of steps thereof may be as follows:

S1: the water inlet system may be fluidly connected to an external water source, after the vehicle 2 that is loaded with the vehicle-mounted system 20 arrives at a designated location, so that water may be input into the heating system through the water inlet system for heating.

S2: the detachable pretreatment chamber 6 may be built near the vehicle-mounted system 20. The temperature and humidity detector 214, the water heating device, and the humidification device may be mounted in the detachable pretreatment chamber 6. The humidification device may be fluidly connected to the humidification system of the vehicle-mounted system 20 through a fifth pipeline (e.g., humidification pipe 73, or the like). The water heating device may be fluidly connected to the heating system of the vehicle-mounted system 20 through a third pipeline (e.g., water inlet pipe 71, or the like).

S3: The items to be sterilized may be placed in the detachable pretreatment chamber 6. Water may be circulated between the heating system and the water heating device to heat the detachable pretreatment chamber 6. The humidification system may humidify the detachable pretreatment chamber 6 through use of the humidification device.

S4: Temperature and humidity in the detachable pretreatment chamber 6 may be monitored in real time using the temperature and humidity detector 214. The monitored temperature and humidity measurements may be transmitted to the automatic control system. The automatic control system may control the humidification device and the water heating device to maintain the detachable pretreatment chamber 6 at a predetermined temperature and humidity depending on the different items to be sterilized.

The mobile pretreatment apparatus 1 of the present disclosure realizes all-weather and all-round (or comprehensive) supporting gas sterilizers, such as ethylene oxide sterilizers, which may be configured for pre-humidifying and pre-heating before sterilizing items to be sterilized and may have features including, but not limited to, fast movement, safety and reliable, convenient assembly and disassembly, and good treatment effect. It may be of great significance to promote the development and application of fast-moving outdoor gas sterilization. The vehicle-mounted system 20 of the present disclosure may provide heating, humidification, and automatic control for the detachable pretreatment chamber 6, which can realize the flexible movement of the sterilization pretreatment chamber 6, and may not be limited by the sterilization site, so that the pretreatment chamber 6 can be quickly moved to the destination, can be mounted, and can be put into use immediately. Both the vehicle-mounted system 20 and the detachable pretreatment chamber 6 may both be mobile independent systems, which can be transported and can participate in work separately or can be used together. The heating method used may be a method of circulating hot water, and the humidification method used may be the atomizer spray method, which makes the pretreatment heating and humidification processes safe and efficient, while the automatic control system may be used to set different pretreatment temperature and humidity depending on the different items to be sterilized. Since the pretreatment chamber 6 may be provided with a modular pretreatment chamber body 61, it can be detached and mounted, which may be convenient for transportation. Therefore, the size of the pretreatment chamber 6 can be adjusted depending on the needs of sterilization. The configuration of the pretreatment chamber body 61, without intermediate column support, can increase the space utilization of the pretreatment chamber 6 to 100%. The pretreatment chamber 6 may adopt the use of reusable thermal insulation materials, which can save energy and can reduce costs, while ensuring the pretreatment effect.

Figure 5:
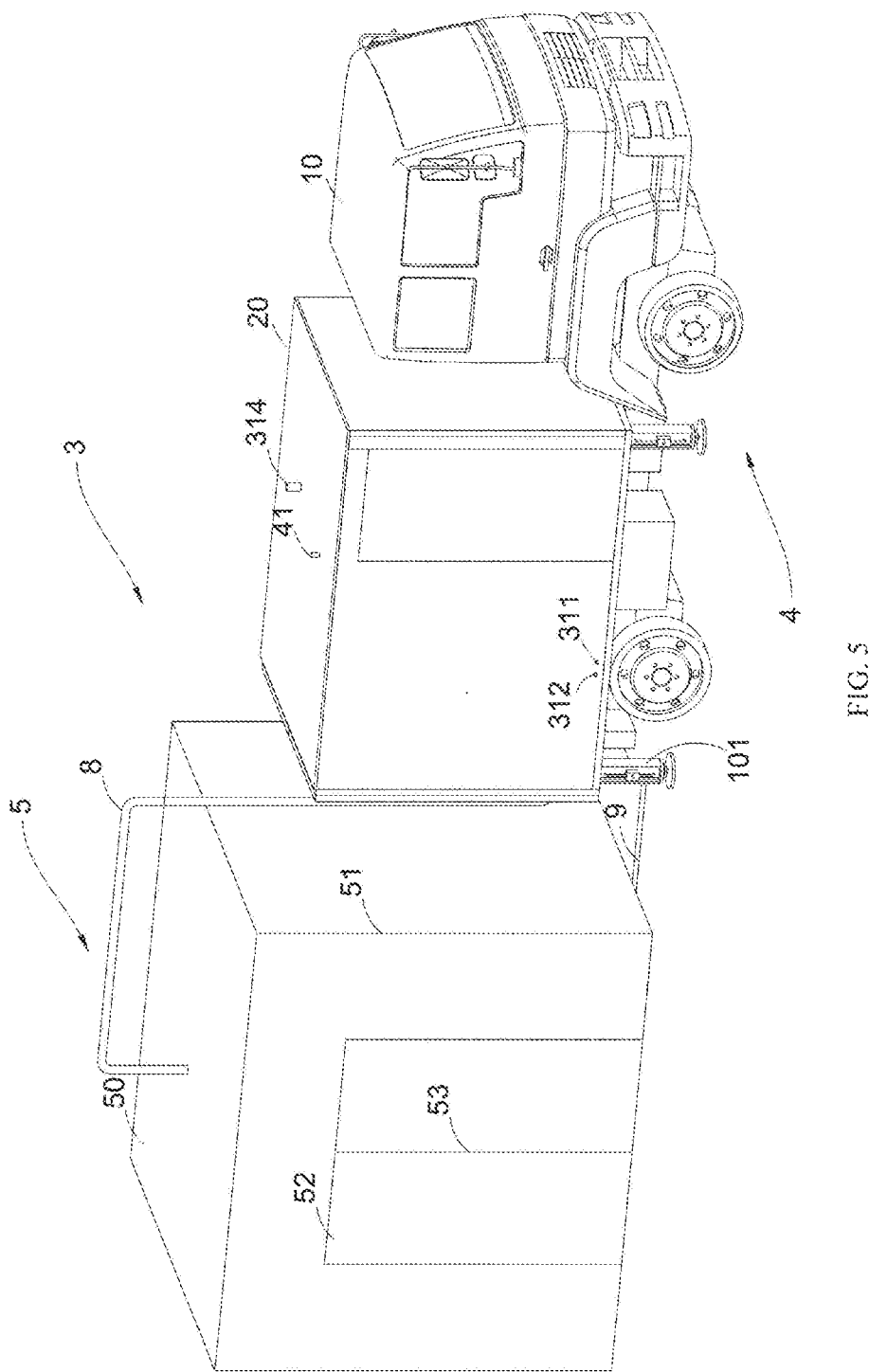
FIG. 5 is a schematic diagram depicting a perspective view of a mobile analysis apparatus according to an embodiment of the present disclosure.
Figure 6:
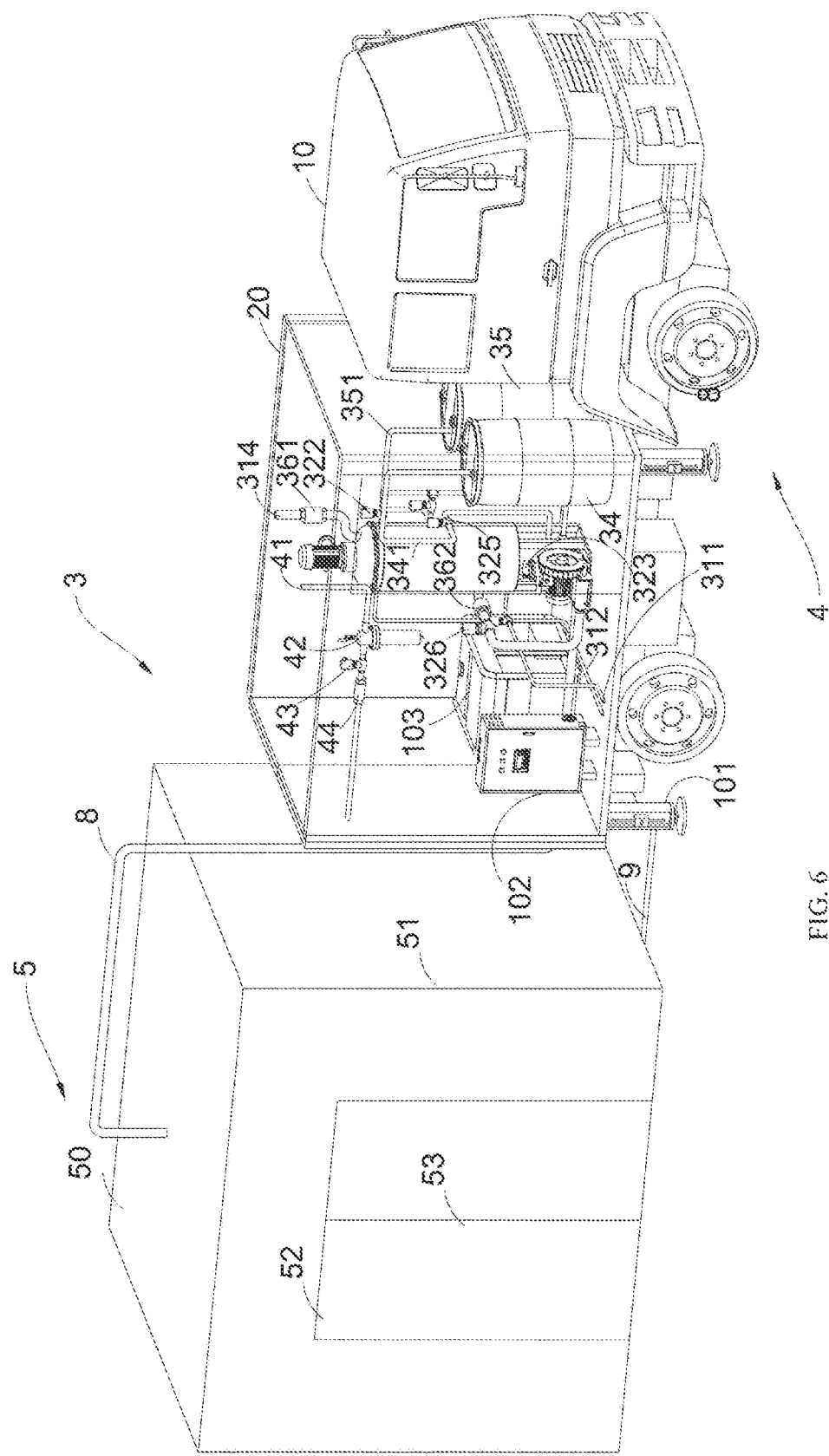
FIG. 6 is a schematic diagram depicting an internal structure of the mobile analysis apparatus of FIG. 5.
Figure 7:
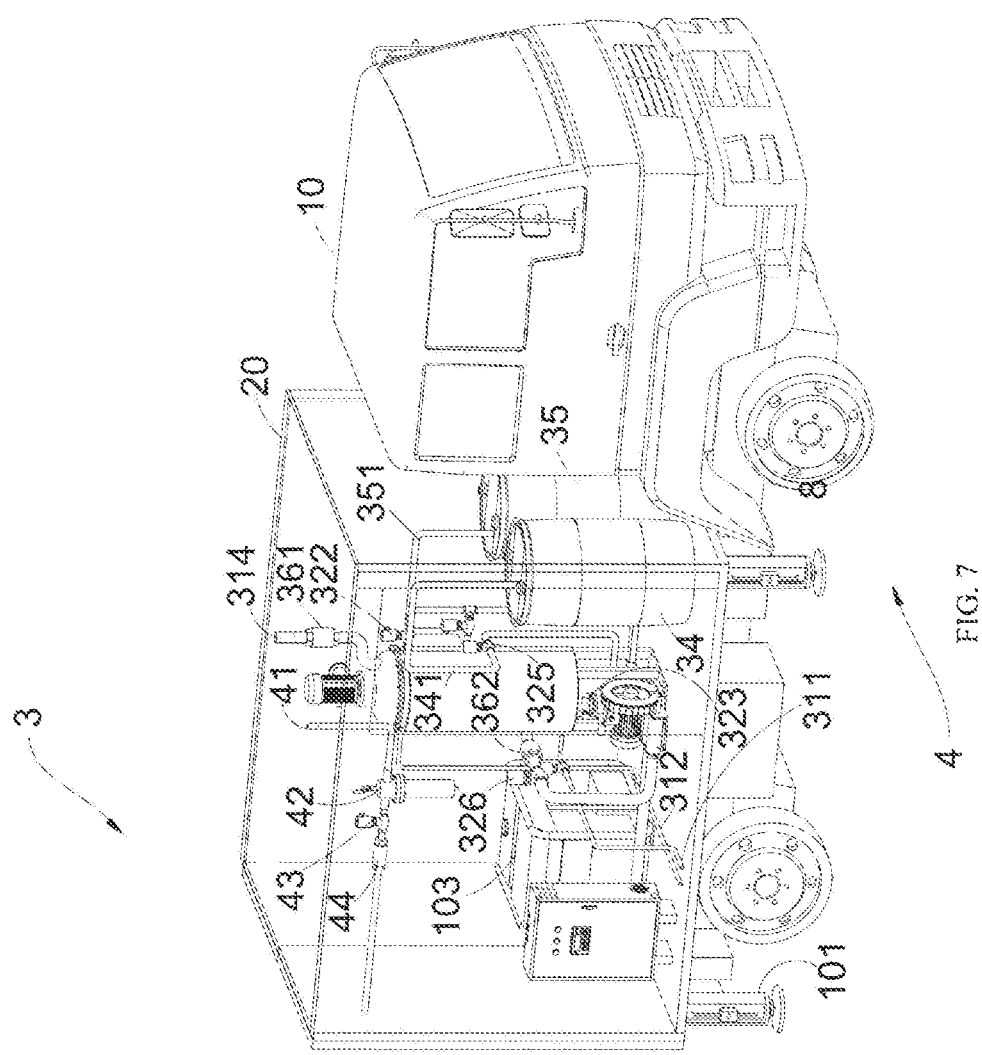
FIG. 7 is a schematic diagram depicting an enlarged view of a vehicle-mounted system of the mobile analysis apparatus of FIG. 6.
Figure 8:
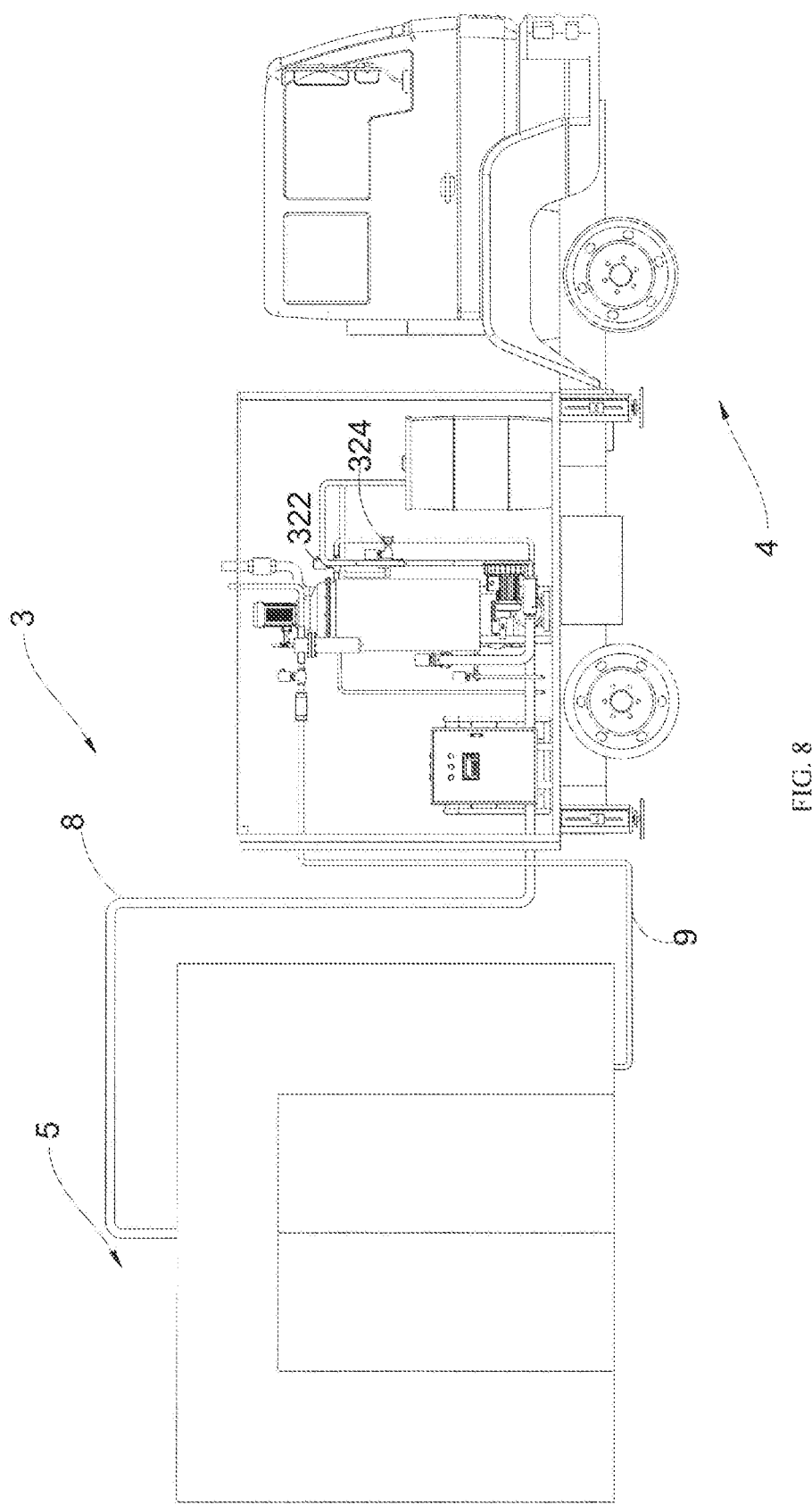
FIG. 8 is a schematic diagram depicting a side view of the mobile analysis apparatus of FIG. 6.
Figure 9:
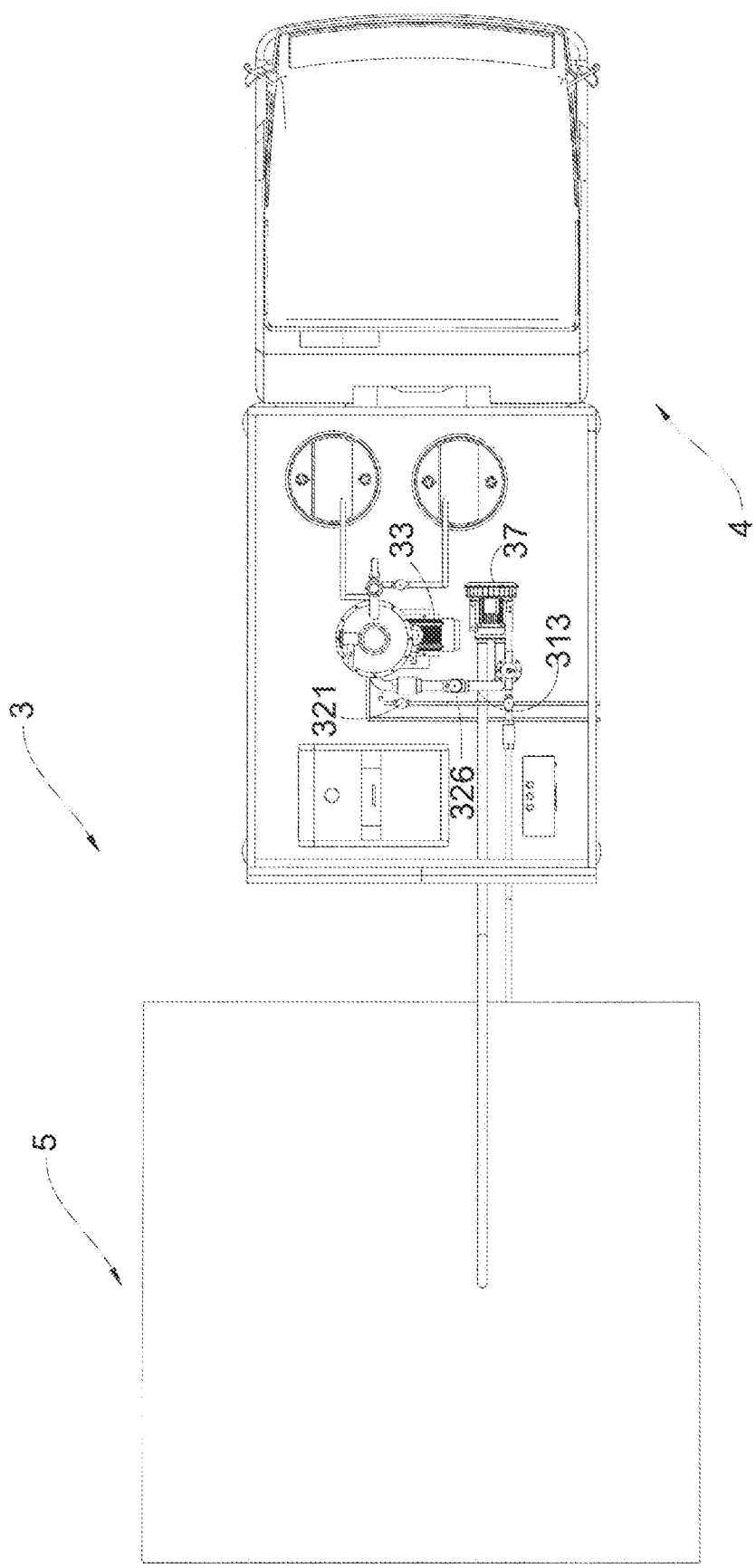
FIG. 9 is a schematic diagram depicting a top view of the mobile analysis apparatus of FIG. 6.

As shown in FIGS. 5 to 9, an embodiment of the present disclosure further provides a mobile analysis apparatus 3, which can be used for analyzing items to be analyzed that have been sterilized using ethylene oxide. The mobile analysis apparatus 3 may include a vehicle-mounted system 20 and a detachable analysis chamber 5. The detachable analysis chamber 5 may be configured to accommodate items to be analyzed. The vehicle-mounted system 20 may be a movable system adapted to be mounted on a vehicle (such as vehicle 4, or the like).

According to some embodiments, vehicle 4 may include, for example, a vehicle-mounted system 20 and a driving system 10. In some implementations, the vehicle-mounted system 20 may be mounted on the vehicle 4. The vehicle-mounted system 20 may be adapted to be driven by the driving system 10. The vehicle-mounted system 20 may include an automatic control system, a harmless gas treatment system, and a fresh air system. The harmless gas treatment system and the fresh air system may each be electrically connected to the automatic control system. The harmless gas treatment system may include a harmless gas treatment device 31 containing a reaction liquid therein. The detachable analysis chamber 5 may be fluidly connected to the harmless gas treatment device 31 through an exhaust pipe 8. The fresh air system can be fluidly connected to the detachable analysis chamber 5 through an intake pipe 9. In some embodiments, the exhaust pipe 8 may be located at the top portion of the detachable analysis chamber 5, while the intake pipe 9 may be located at the bottom portion of the detachable analysis chamber 5.

In some embodiments, the vehicle-mounted system 20 may further include a cargo box that can be loaded on a truck. The automatic control system, the harmless gas treatment system, and the fresh air system may be provided in the cargo box.

In some embodiments, the detachable analysis chamber 5 may include an analysis chamber body 50 (for example, including a foldable supporting frame 51, or the like), at least one feed door 52, and at least one sealing strip 53. In the built detachable analysis chamber 5, the at least one feed door 52 may be mounted on the side wall of the analysis chamber body 50, and the at least one feed door 52 may form a sealed closed space with the analysis chamber body 50 through use of the at least one sealing strip 53. The foldable supporting frame 51 may be, for example, a tent frame, or the like. In some embodiments, the at least one feed door 52 may be a double-opening door, or the like. The at least one sealing strip 53 may be located at the junction of each of the at least one feed door 52 and the analysis chamber body 50. The double-opening feed door 52 may be conducive to loading items to be analyzed (and/or sterilized) and to unloading the analyzed (and/or sterilized) items, resulting in the saving of space and time. The at least one sealing strip 53 can increase the tightness of the detachable analysis chamber 5, can better seal the sterilized items, and can ensure that the sterilized items may be packaged in a sterile state. Moreover, residual analysis gas (such as residual ethylene oxide analysis gas) may be systematically treated through the harmless gas treatment system, and then harmlessly discharged, ensuring the gas-tightness when replacing sterile air, and accelerating the replacing speed of analysis gas in a closed environment, thereby shortening an analyzing time.

In some embodiments, the automatic control system may include a controller 102 and a power supply system 103. The controller 102 may be electrically connected to the harmless gas treatment system and the fresh air system.

In some embodiments, the vehicle 4 may further include at least one supporting device 101. The at least one supporting device 101 may be fixedly connected to a bottom portion of the vehicle-mounted system 20, specifically mounted at the four corners of the bottom portion of the vehicle-mounted system 20, to provide support for the vehicle-mounted system 20 and to maintain stability of the vehicle-mounted system 20 during operation. In some embodiments, the grounding end of each of the at least one supporting device 101 has a gasket, so as to increase the contact area and to improve the supporting stability.

The harmless gas treatment device 31 may be configured such that the introduced analysis gas and the reaction liquid react in the harmless gas treatment device 31, so that the analysis gas may be made harmless. The harmless gas treatment device may include a liquid inlet, a liquid outlet, a gas inlet 313, and a gas outlet 314. The reaction liquid may be input into the harmless gas treatment device 31 through the liquid inlet, and may be discharged through the liquid outlet. The analysis gas may be input into the harmless gas treatment device 31 from the gas inlet 313 and may be discharged through the gas outlet 314. The gas inlet 313 may be fluidly connected to the exhaust pipe 8. The analysis gas and the reaction liquid come into contact and react in the harmless gas treatment device 31.

In an embodiment, the gas inlet 313 may be located at a bottom portion of the harmless gas treatment device 31. The gas outlet 314 may be located at a top portion of the harmless gas treatment device 31.

In an embodiment, the harmless gas treatment system may further include a fresh material storage tank 34 and a waste liquid recovery tank 35. The waste liquid recovery tank 35 may be fluidly connected to the liquid outlet, while the fresh material storage tank 34 may be fluidly connected to the liquid inlet.

In some embodiments, the harmless gas treatment system 31 may further include a circulating pump 33, a feed pipe 341, and a liquid discharge pipe 351. The circulating pump 33 may be fluidly connected to the fresh material storage tank 34 through the feed pipe 341, and may be fluidly connected to the waste liquid recovery tank 35 through the liquid discharge pipe 351.

In some embodiments, the harmless gas treatment system may further include a plurality of valves, a plurality of check valves, and a fan 37. The plurality of valves may include, for example, a fifth valve 324, a sixth valve 325, a seventh valve 326, an eighth valve 322, and a ninth valve 323. The plurality of check valves may include, for example, a second check valve 361 and a third check valve 362.

The fan 37 may be mounted on the exhaust pipe 8, and may be fluidly connected to the detachable analysis chamber 5 through the exhaust pipe 8, and may drive the analysis gas that is in the detachable analysis chamber 5 into the harmless gas treatment device 31 through the exhaust pipe 8.

The seventh valve 326 and the third check valve 362 may be provided on the exhaust pipe 8 between the fan 37 and the gas inlet 313 of the harmless gas treatment device 31. The fan 37 may be fluidly connected to the gas inlet 313 through the seventh valve 326 and the third check valve 362 in sequence. The second check valve 361 may be mounted at the gas outlet 314 of the harmless gas treatment device 31. A first check valve 44 and the second check valve 361 ensure that the flow direction of the analysis gas in the harmless gas treatment device 31 may be a one-way flow from the gas inlet 313 to the gas outlet 314. The fan 37 and the seventh valve 326 may each be electrically connected to the controller 102.

The eighth valve 322 may be mounted at the liquid inlet of the harmless gas treatment device 31. The ninth valve 323 may be mounted at the liquid outlet. The eighth valve 322 and the ninth valve 323 may be in fluid communication with each other through a circulating pipeline. The circulating pump 33 may be mounted on the circulating pipeline. Specifically, the fresh material storage tank 34 may be fluidly connected between the ninth valve 323 and the circulating pump 33 through the feed pipe 341. The sixth valve 325 may be mounted on the feed pipe 341. The waste liquid recovery tank 35 may be fluidly connected between the eighth valve 322 and the circulating pump 33 through the liquid discharge pipe 351. The fifth valve 324 may be mounted on the liquid discharge pipe 351. The circulating pump 33, the eighth valve 322, the ninth valve 323, the fifth valve 324, and the sixth valve 325 may each be electrically connected to the controller 102. The circulating pump 33 may drive the circulation flow of the reaction liquid in the harmless gas treatment device 31 and may drive the replacement of the reaction liquid.

In an embodiment, the harmless gas treatment device 31 may include a hollow interlayer, a water inlet 311, and a water outlet 312, the water inlet 311 and the water outlet 312 being in fluid communication with the hollow interlayer. The hollow interlayer may be configured to circulate cooling water, so that the reaction liquid and the analysis gas can react at a predetermined temperature. A tenth valve 321 may be mounted at the water inlet 311. The tenth valve 321 may be electrically connected to the controller 102. The water inlet 311 and the water outlet 312 may be fluidly connected to a water pipeline of a circulating external water source. Driven by the fan 37, the analysis gas in the detachable analysis chamber 5, such as ethylene oxide analysis gas, or the like, may be transported to the harmless gas treatment device 31 for harmless gas treatment, and may be discharged from the gas outlet 314 after achieving or satisfying the harmless gas discharge standards. At the same time, the fan 37 may drive air to be introduced into the fresh air system, so as to provide sterile air to the detachable analysis chamber 5, to accelerate the gas flow in the detachable analysis chamber 5, and to replace the residual analysis gas in the detachable analysis chamber 5, such as residual ethylene oxide analysis gas, thereby shortening the analysis time.

In some embodiments, the fresh air system may include a fresh air inlet 41, an air filter 42, an eleventh valve 43, and the first check valve 44. The fresh air inlet 41 may be fluidly connected to the air filter 42, while air filter 42 may be fluidly connected to the detachable analysis chamber 5 through the intake pipe 9. The eleventh valve 43 and the first check valve 44 may be provided on the intake pipe 9. The air filter 42 and the eleventh valve 43 may be electrically connected to the controller 102.

An embodiment of the present disclosure provides a method of operating the above described mobile analysis apparatus 3, and a non-limiting example of steps thereof may be as follows:

S1: the detachable analysis chamber 5 may be built near the vehicle-mounted system 20, after the vehicle 4 that is loaded with the vehicle-mounted system 20 arrives at a designated location. The harmless gas treatment system may fluidly connect with the detachable analysis chamber 5 through the exhaust pipe 8. The fresh air system may fluidly connect with the detachable analysis chamber 5 through the intake pipe 9.

S2: the sterilized items to be analyzed may be placed in the detachable analysis chamber 5. The analysis gas from the detachable analysis chamber 5 may be drawn into the harmless gas treatment device 31. Since the analysis gas in the detachable analysis chamber 5 may be drawn out, the gas pressure in the detachable analysis chamber 5 may be reduced. Due to the pressure difference, the sterile air that is processed by the fresh air system may be caused (or directed) to flow into the detachable analysis chamber 5. As a result, the gas replacement may be completed.

S3: the analysis gas may be harmlessly treated by the harmless gas treatment device 31. The residual gas after being treated may be discharged from the harmless gas treatment device 31 to the environment outside the mobile analysis apparatus 3 through the gas outlet 314.

Specifically, in Step S2, under the continuous operation of the fan 37, the gas in the detachable analysis chamber 5 may be continuously drawn into the harmless gas treatment device 31, and the external air may be continuously introduced into the detachable analysis chamber 5 through the fresh air system. In Step S3, the harmless gas treatment device 31 continues to perform harmless gas treatment on the analysis gas until the retention of the sterilized gas in the sterilized items in the detachable analysis chamber 5 reaches a predetermined value, at which point one round of analysis may be completed.

In an embodiment, the method may further include Step S4. After several rounds of analysis, after the reaction liquid in the harmless gas treatment device 31 has been completely consumed, the reaction waste liquid in the harmless gas treatment device 31 may be drawn out, and the fresh reaction liquid may be introduced into the harmless gas treatment device 31, so as to complete the injection of fresh reaction liquid.

In some embodiments, Step S2 may further include actuating the power supply system 103. Under the control of the controller 102, the at least one supporting device 101, the fan 37, the seventh valve 326, the eleventh valve 43, the tenth valve 321, the eighth valve 322, the ninth valve 323, and the circulating pump 33 may be actuated or opened, as appropriate, and the fan 37 may draw the ethylene oxide analysis gas from the detachable analysis chamber 5 into the harmless gas treatment device 31.

In some embodiments, in Step S3, the ethylene oxide analysis gas may be harmlessly treated in the harmless gas treatment device 31. At this time, the fifth valve 324 and the sixth valve 325 may be closed, and the circulating pump 33 may drive the reaction liquid in the harmless gas treatment device 31 to be circulated through a circulation pipeline. The treated harmless gas may be discharged from the gas outlet 314 to the environment outside the mobile analysis apparatus 3, through the second check valve 361. When the harmless gas treatment device 31 operates, cooling water may be introduced into the hollow interlayer of the harmless gas treatment device 31 through the tenth valve 321 through the water inlet 311, so as to cool the harmless gas treatment device 31, and may finally flow out from the water outlet 312.

The mobile analysis apparatus 3 of the present disclosure may include a mobile vehicle-mounted system 20 and a detachable analysis chamber 5 that may be independently mounted and carried, which makes storage, use, and transportation more convenient, and expands the potential range of application or implementation of sterilization technology, such as ethylene oxide gas sterilization technology. Moreover, the system (including the mobile pretreatment apparatus 1 and the mobile analysis apparatus 3, or the like) can sterilize and disinfect items, and can analyze the residual gas (such as ethylene oxide gas) in the items after sterilization by using the sterilizer together in the field, so as to realize rapid analysis of fully automated, harmless gas treatment of the residual sterilized gas in sterilized items, which adapts to all-weather environments and meets the large demand for sterile products for disaster relief and epidemic prevention. The mobile vehicle-mounted system 20 might perform the analysis gas treating task for the analysis gas (for example, ethylene oxide gas). The fan and the fresh air system may be used to evacuate and to replace the gas in the analysis chamber 5, which can increase the amount of ventilation, can facilitate analysis of the residual sterilization gas in sterilized items, and can speed up the treatment of sterilized items to achieve or satisfy the safe use standards, while the residual sterilized gas that may be drawn may be harmlessly treated and discharged after achieving or satisfying the environmental safety discharge standards, so as to ensure the safety of the environment and surrounding life.

Example 1

As shown in FIGS. 1, 2, 3, and 4, the mobile pretreatment apparatus 1 provided by this embodiment may include, without limitation, the pretreatment chamber body 61, the temperature and humidity detector 214, the at least one water heating plate 711, the at least one sealing strip 611, the at least one feed door 610, the at least one humidification sprinkler 612, the controller 102, the power supply system 103, the humidification pipe 73, the first valve 731, the second valve 732, the third valve 723, the fourth valve 714, the atomizer 733, the atomizer replenishment pipe 734, the first filter 722, the second filter 712, the water inlet 721, the electric heating tube(s) 75, the water tank 7, the thermometer 211, the level gauge 18, the circulating water pump 713, the water inlet pipe 71, and the water return pipe 72, and the like.

The mobile pretreatment apparatus might include a vehicle-mounted system 20 and a pretreatment chamber 6.

The vehicle-mounted system 20 may include, but is not limited to, the controller 102, the power supply system 103, the humidification pipe 73, the first valve 731, the second valve 732, the third valve 723, the fourth valve 714, the atomizer 733, the atomizer replenishment pipe 734, the first filter 722, the second filter 712, the water inlet 721, the electric heating tube(s) 75, the water tank 7, the thermometer 211, the level gauge 18, the circulating water pump 713, the water inlet pipe 71, and the water return pipe 72, and the like. The above components may be all arranged and mounted in the vehicle-mounted system 20. The vehicle-mounted system 20 can reach any designated location quickly and flexibly.

The humidification pipe 73, the first valve 731, the atomizer 733, and the atomizer replenishment pipeline 734 that are fluidly connected in sequence in the direction from the at least one humidification sprinkler 612 to the water inlet 721 constitute a humidification system.

The fourth valve 714, the electric heating tube(s) 75, the water tank 7, the thermometer 211, the level gauge 18, the circulating water pump 713, the second filter 712, the water inlet pipe 71, and the water return pipe 72 constitute a heating system. The electric heating tube(s) 75, the thermometer 211, and the level gauge 18 may be arranged and mounted in the water tank 7. The electric heating tube(s) 75 and the level gauge 18 may be mounted at the bottom portion and at the middle-upper portion of the side wall of the water tank 7, respectively, so as to perform heating temperature control and water level monitoring. The circulating water pump 713 may be located between the water tank 7 and the second filter 712. The second filter 712 may be fluidly connected to the pretreatment chamber 6 through the water inlet pipe 71. The water return pipe 72 may be fluidly connect the pretreatment chamber 6 with the water tank 7.

Tap water may be filtered by the first filter 722 through the water inlet 721, and then may be introduced into the water tank 7 and the atomizer 733 to replenish the water tank 7 and the atomizer 733, respectively.

The controller 102 may be configured to control opening and closing of the electromagnetic valves (e.g., the valves, or the like), and to control the operations of each of the atomizer 733, the electric heating tube(s) 75, and the circulating water pump 713, and to process the data obtained by the thermometer 211, the level gauge 18, and the temperature and humidity detector 214, so that automatic control of the entire apparatus can be achieved. At the same time, the power supply system 103 may supply power to the entire apparatus.

The pretreatment chamber 6 may include, without limitation, the pretreatment chamber body 61, the temperature and humidity detector 214, the at least one water heating plate 711, the at least one sealing strip 611, the at least one feed door 610, and the at least one humidification sprinkler 612, and the like. The pretreatment chamber body 61 may be a modular component, which may be transported with the vehicle-mounted system 20, and may be built into a pretreatment chamber 6 at the workplace. The rest of the above components may be arranged in or on the pretreatment chamber 6.

The at least one humidification sprinkler 612 may be mounted on the top portion of the pretreatment chamber 6 and may be fluidly connected to the humidification pipe 73. The atomizer 733 may spray water into the pretreatment chamber 6 through the at least one humidification sprinkler 612 and through the humidification pipe 73, so as to humidify the pretreatment chamber 6.

The at least one water heating plate 711 may be mounted at the bottom portion of the pretreatment chamber 6 and may be fluidly connected to the water return pipe 72. The hot water in the water tank 7 may be introduced to the at least one water heating plate 711 through the water inlet pipe 71 through the circulating water pump 713 and the second filter 712, to heat the pretreatment chamber 6, and may be returned into the water tank 7 through the water return pipe 72, so as to continuously circulate to keep the pretreatment chamber 6 at a constant temperature.

The temperature and humidity detector 214 may be mounted on the side wall of the pretreatment chamber 6 to monitor the temperature and humidity in the pretreatment chamber 6 in real time.

Specifically, the operational process of the mobile pretreatment apparatus 1 as described above may be as follows:

S1: The water inlet 721 in the form of quick-connect snap connector may be fluidly connected to a tap water source, after the vehicle-mounted system 20 has reached, or arrived at, the designated position and has stopped. The controller 102 and the power supply system 103 of the automatic control system may be actuated, the third valve 723 may be controlled to turn on, and the other valves may be controlled to turn off. After being filtered by the water inlet 721 and the first filter 722, the tap water may be injected into the water tank 7. The water level may be monitored by the level gauge 18 until it reaches a predetermined position in the water tank 7.

S2: After the water injection has been completed, the tap water may be turned off, the electric heating tube(s) 75 may be controlled to turn on, so as to heat the water in the water tank 7 to a predetermined temperature. The water temperature may be maintained at a temperature ranging from 40° C. to 80° C., by controlling the electric heating tube(s) 75.

S3: At the same time as Step S2, the pretreatment chamber 6 may start to be built. The splice boards (or other modular components) of the pretreatment chamber body 61 that are carried with the vehicle 4 may be assembled to form the pretreatment chamber 6. Then, the temperature and humidity detector 214, the at least one water heating plate 711, and the at least one humidification sprinkler 612 may be mounted in the pretreatment chamber 6.

S4: After building and assembling the pretreatment chamber 6, the at least one humidification sprinkler 612 may be fluidly connected to the humidification pipe 73. The at least one water heating plate 711 may be fluidly connected to each of the water inlet pipe 71 and the water return pipe 72.

S5: The items to be sterilized may then be placed in the pretreatment chamber 6 through the at least one feed door 610. Then, the at least one feed door 610 may be closed, and sealed with the at least one sealing strip 611.

S6: The pretreatment chamber may then be heated and humidified. The third valve 723 may be controlled to turn off, while the first valve 731, the second valve 732, and the fourth valve 714 may be controlled to turn on. The atomizer 733 and the circulating water pump 713 may then be controlled to be turned on. The water that is atomized by the atomizer 733 may be sprayed into the pretreatment chamber 6 through the at least one humidification sprinkler 612 to humidify the pretreatment chamber 6. The hot water in the water tank 7 may be filtered by the second filter 712 through the circulating water pump 713 and may then be introduced to the at least one water heating plate 711 through the water inlet pipe 71, so as to heat the pretreatment chamber 6. Then, the hot water may be returned into the water tank 7 through the water return pipe 72. In this way, the pretreatment chamber 6 may be continuously heated to be kept at a constant temperature. The temperature and humidity in the pretreatment chamber 6 may be monitored in real-time by the temperature and humidity detector 214, to achieve and maintain a temperature ranging between 40° C. and 80° C. and a humidity ranging between 30% and 80%. If the results were not within the predetermined ranges, the temperature and humidity were adjusted and controlled by the controller 102.

S8: Different temperature and humidity levels may be set depending on the different items to be sterilized, so as to pre-heat and pre-humidify the items to be sterilized before the sterilization, to increase the sterilization effect.

Example 2

As shown in FIGS. 5-9, the mobile analysis apparatus 3 provided by the present disclosure may include, without limitation, the controller 102, the power supply system 103, the harmless gas treatment device 31, the water inlet 311, the water outlet 312, the gas inlet 313, the gas outlet 314, the tenth valve 321, the eighth valve 322, the ninth valve 323, the fifth valve 324, the sixth valve 325, the seventh valve 326, the circulation pump 33, the fresh material storage tank 34, the feed pipe 341, the waste liquid recovery tank 35, the liquid discharge pipe 351, the second check valve 361, the third check valve 362, the fan 37, the fresh air inlet 41, the air filter 42, the eleventh valve 43, the first check valve 44, the foldable supporting frame 51, the at least one feed door 52, the at least one sealing strip 53, the exhaust pipe 8, and the intake pipe 9, and the like.

The entire mobile analysis apparatus 3 may include vehicle-mounted system 20 and analysis chamber 5.

The vehicle-mounted system 20 may include, but is not limited to, the controller 102, the power supply system 103, the harmless gas treatment device 31, the water inlet 311, the water outlet 312, the gas inlet 313, the gas outlet 314, the tenth valve 321, the eighth valve 322, the ninth valve 323, the fifth valve 324, the sixth valve 325, the seventh valve 326, the circulating pump 33, the fresh material storage tank 34, the feed pipe 341, the waste liquid recovery tank 35, the liquid discharge pipe 351, the second check valve 361, the third check valve 362, the fan 37, the fresh air inlet 41, the air filter 42, the eleventh valve 43, and the first check valve 44, and the like. The above components may be all arranged and mounted on the vehicle-mounted system 20. The vehicle-mounted system 20 can reach any designated location quickly and flexibly.

The fresh air inlet 41, the air filter 42, the eleventh valve 43, and the first check valve 44 may be fluidly connected in sequence to form a fresh air system. The fresh air system may be fluidly connected to the analysis chamber 5 through the intake pipe 9 to supply sterile air to the analysis chamber 5.

The harmless gas treatment device 31, the water inlet 311, the water outlet 312, the gas inlet 313, the gas outlet 314, the tenth valve 321, the eighth valve 322, the ninth valve 323, the fifth valve 324, the first six valve 325, the seventh valve 326, the circulating pump 33, the fresh material storage tank 34, the feed pipe 341, the waste liquid recovery tank 35, the liquid discharge pipe 351, the second check valve 361, the third check valve 362, and the fan 37 constitute a harmless gas treatment system. The fan 37 may be mounted between the analysis chamber 5 and the harmless gas treatment device 31, and may be fluidly connected to the analysis chamber 5 through an exhaust pipe 8. The ethylene oxide analysis exhaust gas from the analysis chamber 5 may be drawn into the harmless gas treatment device 31 to be subjected to harmless gas treatment.

The controller 102 may be configured to control opening and closing of the valves, and to control the operations of each of the circulating pump 33 and the fan 37 to realize automatic control of the entire apparatus, while the power supply system 103 supplies power to the entire apparatus.

The analysis chamber 5 may include, but is not limited to, the foldable supporting frame 51, the at least one feed door 52, and the at least one sealing strip 53. The at least one feed door 52 may be mounted on the side wall of the foldable supporting frame 51. The at least one feed door 52 and the foldable supporting frame may be sealed and closed through the at least one sealing strip 53 to forms the analysis chamber 5. The analysis chamber 5 may be a modular component that may be transported with the vehicle-mounted system 20 and built in the workplace when needed.

The exhaust pipe 8 may be fluidly connected to the top portion of the analysis chamber 5, while the intake pipe 9 may be fluidly connected to the bottom portion of the analysis chamber 5.

Specifically, the operational process of the mobile analysis apparatus 3 may be as follows:

S1: A driving system 10 may be started, and the vehicle-mounted system 20 that is mounted on the vehicle 4 may be parked at the designated workplace for sterilization. The analysis chamber 5 may be built nearby.

S2: After building and assembling the analysis chamber 5, the exhaust pipe 8 and the intake pipe 9 may each be fluidly connected between the vehicle-mounted system 20 and the analysis chamber 5.

S3: The items to be sterilized may be placed in the analysis chamber 5 through the at least one feed door 52, and then the at least one feed door 52 may be closed, and may be sealed with the at least one sealing strip 53.

S4: The analysis may then be started. After actuating the power supply system 103, the at least one supporting device 101, the fan 37, and the seventh valve 326 may be turned on or opened, as appropriate, under the control of the controller 102, while the eleventh valve 43, the tenth valve 321, the eighth valve 322, the ninth valve 323, and the circulating pump 33 may be turned off or closed, as appropriate, under the control of the controller 102. The fan 37 may draw the ethylene oxide analysis gas in the analysis chamber 5 into the harmless gas treatment device 31.

S5: The ethylene oxide analysis gas that is in the analysis chamber 5 may be drawn out, and the gas pressure therein may be reduced. Due to the pressure difference, the air may be introduced from the fresh air inlet 41 and may be filtered by the air filter 42 to form sterile air. The sterile air may flow into the analysis chamber 5, resulting in the gas replacement being completed.

S6: The ethylene oxide analysis gas may be harmlessly treated in the harmless gas treatment device 31. At this time, the fifth valve 324 and the sixth valve 325 may be closed. The circulating pump 33 may circulate the reaction liquid in the harmless gas treatment device 31 through the circulation pipeline. The treated harmless gas may be discharged from the gas outlet 314 through the second check valve 361. When the harmless gas treatment device 31 is in operation, cooling water may be introduced from the water inlet 311 through the tenth valve 321 into the hollow interlayer of the harmless gas treatment device 31, so as to cool the harmless gas treatment device 31, and may finally flow out of the water outlet 312.

S7: Steps S4 to S6 may be repeated until the residual ethylene oxide in the sterilized items in the analysis chamber 5 has reached the safety value of the relevant standards. The fan 37, the eleventh valve 43, the tenth valve 321, the eighth valve 322, the ninth valve 323, and the circulating pump 33 may be turned off or closed, as appropriate, at which point a round of analysis may be ended.

S8: The qualified sterilized items after analysis may be unloaded from the analysis chamber 5 through the at least one feed door 52, and then the at least one feed door 52 may be closed.

S9: After several rounds of analysis, when the reaction liquid in the harmless gas treatment device 31 has been completely consumed, the circulating pump 33, the ninth valve 323, and the fifth valve 324 may be turned on or opened, as appropriate. The circulating pump 33 may introduce the reaction waste liquid from the harmless gas treatment device 31 into the circulating pipeline and the liquid discharge pipe 351, so as to introduced it into the waste liquid recovery tank 35 through the liquid outlet. The ninth valve 323 and the fifth valve 324 may be closed to complete the waste liquid discharge process. The eighth valve 322 and the sixth valve 325 may be opened, allowing the circulating pump 33 to introduce the fresh reaction liquid that is contained in the fresh material storage tank 34 into the feed pipe 341 and the circulating pipeline, so as to introduce it into the harmless gas treatment device 31 from the liquid inlet. The circulating pump 33, the eighth valve 322, the sixth valve 325, and the seventh valve 326 may be turned off or closed, as appropriate, to complete the injection of the fresh liquid. Otherwise, Steps S4 to S7 may be repeated.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments described above, it will be appreciated that the invention is intended to cover all modifications and equivalents within the scope of the following claims.

What is claimed is:

1. A mobile analysis apparatus, comprising:
   a detachable analysis chamber configured to accommodate items to be analyzed; and
   a vehicle-mounted system adapted to be mounted on a vehicle;
   wherein the vehicle-mounted system comprises an automatic control system, a harmless gas treatment system, and a fresh air system, wherein the harmless gas treatment system and the fresh air system are each electrically connected to the automatic control system;
   wherein the harmless gas treatment system comprises a harmless gas treatment device; and
   wherein the detachable analysis chamber is fluidly connected to the harmless gas treatment device through an exhaust pipe, and is fluidly connected to the fresh air system through an intake pipe.

2. The mobile analysis apparatus according to claim 1, wherein the detachable analysis chamber comprises an analysis chamber body, at least one feed door, and at least one sealing strip; and wherein, in the detachable analysis chamber, the at least one feed door is mounted on a side wall of the analysis chamber body, and forms a sealed closed space with the analysis chamber body through use of the at least one sealing strip.

3. The mobile analysis apparatus according to claim 1, wherein:
- the harmless gas treatment device comprises a liquid inlet, a liquid outlet, a gas inlet, and a gas outlet, and is configured such that introduced analysis gas and reaction liquid react in the harmless gas treatment device;
- the harmless gas treatment system further comprises a fresh material storage tank and a waste liquid recovery tank, the waste liquid recovery tank being fluidly connected to the liquid outlet, and the fresh material storage tank being fluidly connected to the liquid inlet; and
- the gas inlet is fluidly connected to the exhaust pipe.

4. The mobile analysis apparatus according to claim 3, wherein the harmless gas treatment system further comprises a circulating pump, a feed pipe, and a liquid discharge pipe; and wherein the circulating pump is fluidly connected to the fresh material storage tank through the feed pipe, and is fluidly connected to the waste liquid recovery tank through the liquid discharge pipe.

5. The mobile analysis apparatus according to claim 4, wherein:
- the harmless gas treatment system further comprises a fifth valve, a sixth valve, a seventh valve, an eighth valve, a ninth valve, a second check valve, a third check valve, and a fan;
- the fan is mounted on the exhaust pipe, and drives the introduced analysis gas that is in the detachable analysis chamber into the harmless gas treatment device through the exhaust pipe;
- the seventh valve and the third check valve are provided on the exhaust pipe between the fan and the gas inlet;
- the second check valve is mounted at the gas outlet;
- the eighth valve is provided at the liquid inlet and the ninth valve is provided at the liquid outlet;
- the sixth valve is provided on the feed pipe;
- the fifth valve is provided on the liquid discharge pipe; and
- the fan, the circulating pump, and the fifth valve through the ninth valve are each electrically connected to the automatic control system.

6. The mobile analysis apparatus according to claim 1, wherein:
- the harmless gas treatment device comprises a hollow interlayer, a water inlet, and a water outlet, the water inlet and the water outlet being fluidly connected to the hollow interlayer, and the hollow interlayer being configured to circulate cooling water; and
- the harmless gas treatment system further comprises a tenth valve provided on the water inlet of the harmless gas treatment device, the tenth valve being electrically connected to the automatic control system.

7. The mobile analysis apparatus according to claim 1, wherein:
- the fresh air system comprises an air filter, an eleventh valve, and a first check valve;
- the air filter is fluidly connected to the detachable analysis chamber through the intake pipe;
- the eleventh valve and the first check valve are provided on the intake pipe; and
- the air filter and the eleventh valve are electrically connected to the automatic control system.

8. The mobile analysis apparatus according to claim 1, wherein the automatic control system comprises a controller and a power supply system, for respectively providing automatic control and power for the mobile analysis apparatus, wherein the power supply system is electrically connected to the controller.

9. The mobile analysis apparatus according to claim 1, further comprising:
- the vehicle, the vehicle comprising the vehicle-mounted system, a driving system, and at least one supporting device;
- wherein the at least one supporting device is configured to be fixedly connected to a bottom portion of the vehicle-mounted system, to provide support for the vehicle-mounted system, and to maintain stability of the vehicle-mounted system during operation.

* * * * *